United States Patent
Zhang et al.

(10) Patent No.: US 10,234,436 B2
(45) Date of Patent: Mar. 19, 2019

(54) GAS CHROMATOGRAPHY-ION MOBILITY SPECTROMETRY APPARATUS

(71) Applicant: Nuctech Company Limited, Haidian District, Beijing (CN)

(72) Inventors: Qingjun Zhang, Beijing (CN); Yuanjing Li, Beijing (CN); Ziran Zhao, Beijing (CN); Weiping Zhu, Beijing (CN); Huishao He, Beijing (CN); Qiufeng Ma, Beijing (CN); Xiang Zou, Beijing (CN); Biao Cao, Beijing (CN)

(73) Assignee: Nuctech Company Limited, Haidian District, Beijing (CN)

( * ) Notice: Subject to any disclaimer, the term of this patent is extended or adjusted under 35 U.S.C. 154(b) by 0 days.

(21) Appl. No.: 15/827,703

(22) Filed: Nov. 30, 2017

(65) Prior Publication Data
US 2018/0164262 A1    Jun. 14, 2018

(30) Foreign Application Priority Data

Dec. 8, 2016   (CN) .......................... 2016 1 1127320

(51) Int. Cl.
| G01N 30/64 | (2006.01) |
| G01N 27/62 | (2006.01) |
| H01J 49/06 | (2006.01) |
| G01N 30/02 | (2006.01) |

(52) U.S. Cl.
CPC .......... *G01N 30/64* (2013.01); *G01N 27/622* (2013.01); *H01J 49/062* (2013.01); *G01N 2030/025* (2013.01)

(58) Field of Classification Search
USPC ........................................ 250/286, 281, 282
See application file for complete search history.

(56) References Cited

U.S. PATENT DOCUMENTS 8,921,774 B1 * 12/2014 Brown ..................... H01J 49/26
250/282
2007/0258861 A1 * 11/2007 Barket, Jr. .......... H01J 49/0022
422/89

* cited by examiner

*Primary Examiner* — Kiet T Nguyen
(74) *Attorney, Agent, or Firm* — Merchant & Gould P.C.

(57) ABSTRACT

The present disclosure provides a gas chromatography-ion mobility spectrometry apparatus, including a housing, an injection port mounted to and connected with the housing and configured for input of a gas containing a sample therein, a multicapillary column configured for separation of a gas substance and an ion mobility tub configured for analysis of the gas substance. The gas chromatography-ion mobility spectrometry apparatus further includes: a gas path part connected with the ion mobility tube and configured for providing the gas to the ion mobility tube and receiving a gas discharged from the ion mobility tube; and a buffer base part detachably mounted to the housing and configured to isolation vibration outside the buffer base part, the ion mobility tube being disposed on the buffer base part, wherein the gas path part is mounted in an interior space of the buffer base part.

10 Claims, 2 Drawing Sheets

GAS CHROMATOGRAPHY-ION MOBILITY SPECTROMETRY APPARATUS

CROSS-REFERENCE TO RELATED APPLICATION

The present application claims priority to Chinese Patent Application No. 201611127320.9, filed on Dec. 8, 2016, entitled "GAS CHROMATOGRAPHY-ION MOBILITY SPECTROMETRY APPARATUS", which is incorporated herein by reference in its entirety.

TECHNICAL FIELD

The present disclosure relates to the field of detection and analysis technologies, and particularly, to a gas chromatography-ion mobility spectrometer (GC-IMS) hyphenated apparatus.

DESCRIPTION OF THE RELATED ART

Gas chromatography-ion mobility spectrometer hyphenated technique has both advantages of gas chromatography (GC) such as a strong separation capacity and advantages of ion mobility spectrometry (IMS) such as a high sensitivity, a high resolution, a fast response speed and the like, and has received adequate attention and has been rapidly developed in the detection and analysis field in recent years.

The gas chromatography-ion mobility spectrometry technique is related to both the gas chromatography and the ion mobility spectrometry, and includes pressure and flow controller(s), a gas purification device, a gas pump, an injection port, a chromatographic column/column box/sleeve, a mobility tube, high pressure, a front-end amplifier circuit, a heating circuit, a central control circuit and the like, there are various of components, which results in complex connection and difficulty in maintenance of the apparatus and meanwhile results in that a signal reaching a Faraday's disc through a drift electrode is extremely weak ($10^{-13}$ C), and that a signal of a detector will be significantly affected by a pulsed gas flow of a diaphragm pump, a vibration between a fan and a cabinet, external electromagnetic interference and the like. In addition, since the ion mobility spectrometry has a very high detection sensitivity (in an order of ppb to ppt), and a pure gas in a detector chamber or pipe will be exchanged with ambient gas after the gas chromatography-ion mobility spectrometry in a flowing gas working mode is separated from a gas source, a stable spectrum shape may be obtained only after a long time gas purification when reconnection is started up, reducing work efficiency. The above factors are not advantageous to mass production and popularization of the gas chromatography-ion mobility spectrometry technique.

SUMMARY

According to an aspect of the present disclosure, there is provided a gas chromatography-ion mobility spectrometry apparatus, comprising a housing, an injection port mounted to and connected with the housing and configured for input of a gas containing a sample therein, a multicapillary column configured for separation of a gas substance and an ion mobility tub configured for analysis of the gas substance; wherein the gas chromatography-ion mobility spectrometry apparatus further comprises:

a gas path part connected with the ion mobility tube and configured for providing the gas to the ion mobility tube and receiving a gas discharged from the ion mobility tube; and a buffer base part detachably mounted to the housing and configured to isolation vibration outside the buffer base part, the ion mobility tube being disposed on the buffer base part, wherein the gas path part is mounted in an interior space of the buffer base part.

DETAILED DESCRIPTION OF PREFERRED EMBODIMENTS

Figure 1:
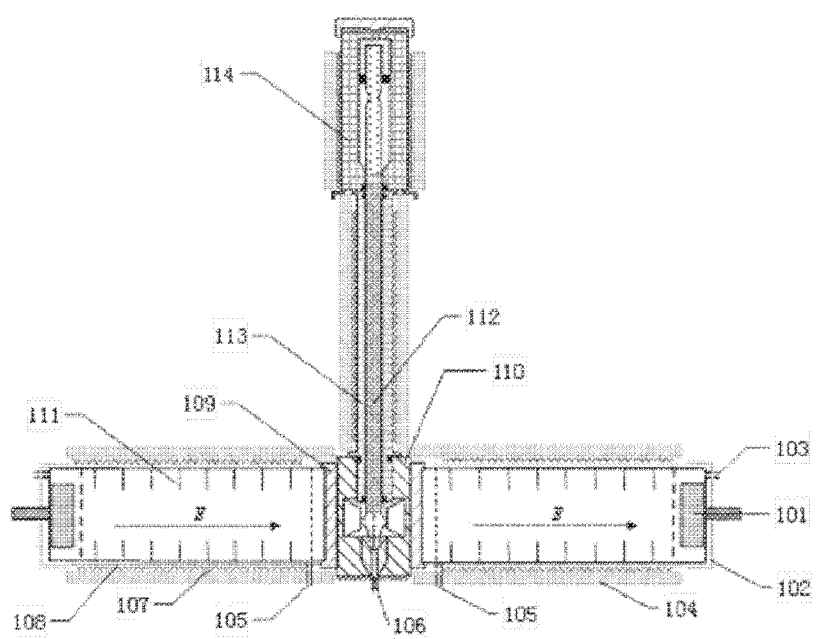
FIG. 1 is a schematic diagram showing an injection port, a multicapillary column and an ion mobility tube of a gas chromatography-ion mobility spectrometry apparatus according to an exemplary embodiment of the present disclosure.

Although various modification and alternative forms are allowable by the present disclosure, exemplary embodiments of the present disclosure are illustrated in the drawings as examples and will be described in detail herein. However, it will be appreciated that the accompanying drawings and detailed description are not intended to limit the present disclosure to the disclosed specific forms, but rather, are intended to cover all modification, equivalents and alternatives falling within spirit and scope of the present disclosure defined in attached claims. The drawings are illustrative and thus are not drawn to scale.

Embodiments of the present disclosure will be described below with reference to the drawings.

An embodiment of the present disclosure provides a gas chromatography-ion mobility spectrometry apparatus 100, comprising a housing 136, an injection port 144 mounted to and connected with the housing 136 and configured for input of a gas containing a sample therein, a multicapillary column 112 configured for separation of a gas substance and an ion mobility tub 111 configured for analysis of the gas substance. The gas chromatography-ion mobility spectrometry apparatus further comprises: a gas path part connected with the ion mobility tube 111 and configured for providing the gas to the ion mobility tube 111 and receiving a gas discharged from the ion mobility tube; and a buffer base part 120 detachably mounted to the housing 136 and configured to isolation vibration outside the buffer base part 120, the ion mobility tube is disposed on the buffer base part 120, wherein the gas path part is mounted in an interior space of the buffer base part 120. The buffer base part 120, together with components disposed inside of the buffer base part, can be conveniently detached from the housing, such that maintenance or replacement of the components is very convenient. In this embodiment, the gas path part is disposed in the interior space of the buffer base part and thus is isolated from the outside without being affected by external impurities and vibration, and may be detached and separated together with the buffer base part from the housing, thus its maintenance is simple.

In this embodiment, the gas chromatography-ion mobility spectrometry apparatus may comprise both gas chromatography part and ion mobility spectrometry part. The gas chromatography part may comprise the injection port 114 and a chromatographic column, which may be a capillary chromatographic column or a multicapillary column 112. The gas chromatography part may further comprise a chromatography gas path, a chromatographic column sleeve and the like. Attachments of chromatographic column may include a chromatographic column box or a chromatographic column sleeve, and in this embodiment, may be a multicapillary column sleeve 113 which has a high column efficiency and a fast separation speed. The multicapillary column 112 is heated for heat preservation under protection of the multicapillary column sleeve 113, and meanwhile the multicapillary column sleeve 113 is further used for a seal connection between the multicapillary column 112 and the injection port 114 and a seal connection between the multicapillary column 112 and the mobility tube 111. The ion mobility spectrometry part comprises the ion mobility tube 111, which has a positive mode in which a positive voltage is applied across ends of the mobility tube for detection of substances such as drugs, and a negative mode in which a negative high voltage is applied across the ends of the mobility tube for detection of explosive samples such as TNT and the like.

The mobility tube may be integrally sintered ceramic mobility tube, because an integrally sintering process can provide the mobility tube with resistance to high temperature and better sealability and shock resistance, which is beneficial for detection and analysis of the detected sample. In others embodiments, ion mobility tube 111 may be also other forms of ion mobility tubes.

In this embodiment, the injection port 114 may be an injection port which is switchable between a diverting mode and a non-diverting mode.

In one embodiment of the present disclosure, the gas chromatography-ion mobility spectrometry apparatus may comprise an intermediate connection body 110 configured for butt-jointing positive and negative mode ion mobility tubes, for seal connection between the chromatographic column and the ion mobility tube 111, and for fixing of the chromatographic column-ion mobility tube. Middles portions of the seal connections between the intermediate connection body and the multicapillary column 112 and between the intermediate connection body and the multicapillary column sleeve 113 may be made of a metal having a passivated surface and a good thermal conductivity, such as copper, so as to avoid chromatographic tailing. Further, in order to ensure insulation between the positive and negative modes and sealing of the mobility tube and still in order to avoid mutual interference between voltages or electric fields, two side portions of the intermediate connection body is made of an insulation material has a resistance to high temperature, a good insulating property and a small expansion coefficient, such as compact type PTFE/PEEK material, and the metal portions are grounded.

Figure 3:
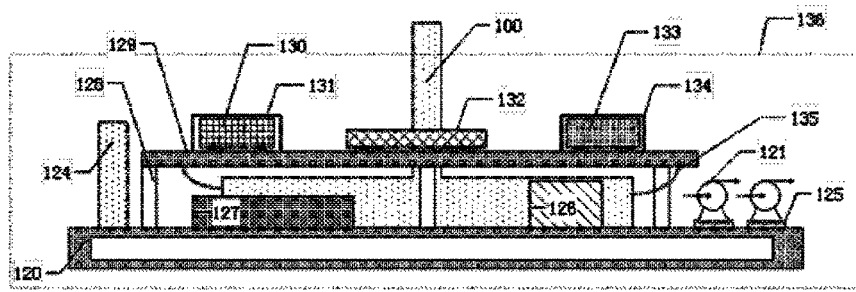
FIG. 3 is schematic diagram showing arrangement of a gas chromatography-ion mobility spectrometry apparatus according to an embodiment of the present disclosure.

In one embodiment of the present disclosure, the buffer base part 120 is made of stainless steel or duralumin so as to isolate interferences such as vibration outside the buffer base part 120, and may be provided with an interior space, such that the gas path part is mounted in the interior space of the buffer base part 120 (as shown in FIG. 3). The buffer base part 120 is further used for mounting and fixing of the gas chromatography-ion mobility spectrometer and components associated therewith.

In one embodiment, the gas chromatography-ion mobility spectrometry apparatus 100 further comprises a circuit control part configured to control operation of the gas chromatography-ion mobility spectrometry apparatus 100, wherein the whole circuit control part is disposed on a portion of the buffer base part 120 above the interior space and arranged such that it is allowed to be separated from the gas path part. It is advantageous that the whole circuit control part is disposed on the portion of the buffer base part above the interior space and arranged such that it is allowed to be separated from the gas path part, so that when the circuit control part needs to be maintained, the housing may be opened to allow maintenance of the circuit control part, without being affected by the gas path part, thereby the maintenance is easier; when the gas path part needs to be maintained, the whole circuit control part may be removed, such that maintenance or replacement of the gas path part is simpler and easier; separate arrangement of the circuit control part and the gas path part is advantageous such that they will interfere with each other, and the circuit control part will not be affected by gas leakage or water vapor and thus is prolonged in service light and improved in reliability.

Figure 2:
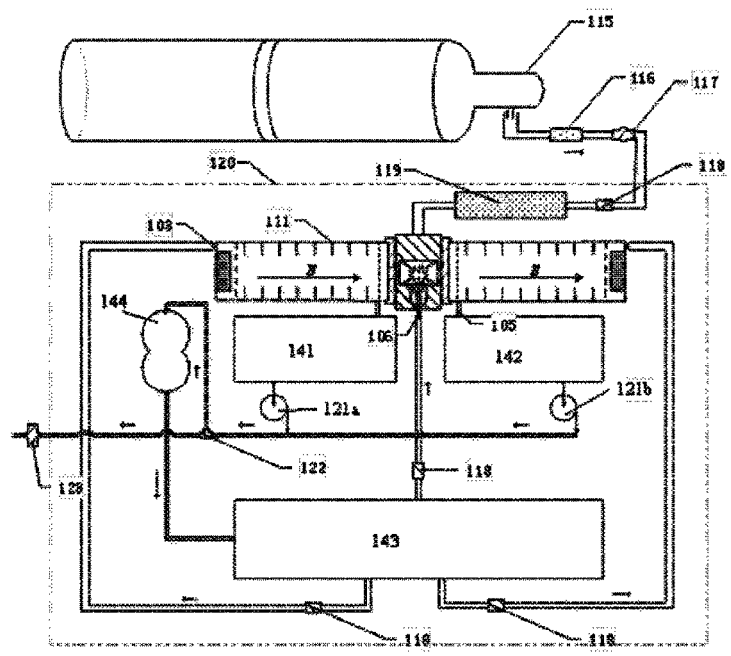
FIG. 2 is a schematic diagram showing a gas path part of a gas chromatography-ion mobility spectrometry apparatus according to an embodiment of the present disclosure.

In one embodiment, the gas path part of the gas chromatography-ion mobility spectrometry apparatus 100 has a chamber configuration including a first buffer chamber and a second buffer chamber, which are in communication with a negative-mode discharge gas interface and a positive-mode discharge gas interface of the ion mobility tube respectively so as to receive gas discharged from the negative-mode discharge gas interface and the positive-mode discharge gas interface respectively. As shown in FIG. 2, a negative-mode discharge gas interface 105 is firstly connected with the first buffer chamber 141 and then with a gas pumping interface of a diaphragm pump 121; a positive-mode discharge gas interface 105 is firstly connected with the second buffer chamber 142 and then with the gas pumping interface of the diaphragm pump 121. Due to the first buffer chamber and second buffer chamber, a pulsed gas flow from the diaphragm pump will not produce pulse interference in movement of the gas in the ion mobility tube in positive and negative modes, such that a signal of the mobility tube is more stable.

In one embodiment of the present disclosure, the gas path part further comprises a third buffer chamber 143, at least part of the gas discharged from the first buffer chamber 141 and the second buffer chamber 142 flows into the third buffer chamber 143, and at least a part of the gas discharged from the third buffer chamber 143 is inputted as an auxiliary injection gas into the ion mobility tube. As shown, discharged gas from the positive and negative mode ion mobility tubes gather at a tee 122, and then a portion of the discharged gas is discharged to the outside via a valve 123 (a flow of discharged gas at the valve 123 substantially equals to a chromatographic injection carrier gas flow), and another portion of the discharged gas enter, after being purified through the molecular sieve 144, the third buffer chamber 143, then divided into three paths, which become, under control of a flow controller 118, in communication with migration gas interfaces 103 of the positive and negative mode ion mobility tubes respectively so as to form a migration gas, and in communication with an auxiliary injection interface 106 of an intermediate connection disc so as to form an auxiliary injection gas for the ion mobility tube.

In this embodiment, the gas path part may further comprise a molecular sieve 144 disposed upstream of the third buffer chamber 143 such that the gas discharged from the first buffer chamber 141 and the second buffer chamber 142 flows into the third buffer chamber 143 after being filtered and purified by the molecular sieve. The gas path part may further comprise a first diaphragm pump 121a and a second diaphragm pump 121b respectively located downstream of the first buffer chamber 141 and the second buffer chamber 142 and respectively connected with the first buffer chamber 141 and the second buffer chamber 142. In order to reduce vibration generated during operations of the first diaphragm pump 121a and the second diaphragm pump 121b, a damping cushion 125 and a damping bolt are used for connections between the first diaphragm pump 121a and the second diaphragm pump 121b and the buffer base part 120.

In this embodiment, the first buffer chamber 141, the second buffer chamber 142 and the third buffer chamber 143 are sealable independently by means of valves, and each buffer chamber has a volume which may be at least five times of the volume of the ion mobility tube 111. In one embodiment, the volume of the third buffer chamber is larger than those of the first and second buffer chambers. In one embodiment, the volume of the third buffer chamber is at least five times of the volume of the ion mobility tube 111. In one embodiment, the volume of the third buffer chamber is more than two times of the volumes of the first and second buffer chambers.

In this embodiment, the gas path part of the gas chromatography-ion mobility spectrometry apparatus 100 comprises at least three buffer chambers which are sealable independently, wherein the first and second buffer chambers (the first diaphragm pump 121a and the second diaphragm pump 121b) are used for connections between the positive and negative-mode discharge gas interfaces and the gas pumping interface of the gas pump, and the third buffer chamber 143 is used for intensively collecting pure gas purified by the molecular sieve. A flow controller is provided at a gas outlet of the third buffer chamber 143 so as to control and adjust flows of the migration gas in the positive and negative modes and the flow of the auxiliary injection carrier gas of the intermediate connection body.

According to embodiments of the present disclosure, the buffer chambers can effectively reduce influence of the pulsed gas flow and instrument vibration on the gas flow in the mobility tube during operations of valves of the first diaphragm pump 121a and the second diaphragm pump 121b, such that an output signal of the gas chromatography-ion mobility spectrometer has more smooth baseline. Arrangement of a number of buffer chambers enables the ion mobility spectrometer to independently control and adjust gas flows for substances of different affinities, thereby achieving optimized detection and analysis of corresponding substances. Purified recovery gas is utilized as the migration gas and the auxiliary injection carrier gas such that consumption of the gas may be effectively reduced.

In an embodiment of the present disclosure, concealed conduits are laid in the buffer base part 120 and configured for connections of gas paths for the ion mobility spectrometry and the gas chromatography, ends of the concealed conduits are connected with external devices (molecular sieve, gas pump and the like) by using quick connections, so that connections of gas paths are simplified, and the interior of the apparatus is clean and aesthetic. In addition, the buffer base part 120 is further used for mounting and fixing of the mobility tube 111, a power supply, circuits and the like. In this embodiment, during installation and debugging of the apparatus, the installation and debugging may be firstly performed on the buffer base part 120, and after the installation and debugging, the buffer base part 120 and the whole apparatus are mounted within the housing 136; during maintenance, the buffer base part 120 and components mounted on the buffer base part 120 may be removed as a whole from the housing of the apparatus, which greatly facilitates installation, debugging and maintenance of the apparatus.

In other embodiments of the present disclosure, the circuit control part may comprise, for example, a power supply module 127, mainboard 129, a preamplifier module 133, a high voltage module 130, a heating module 132, a control module 132 and the like, and these module may be disposed on the buffer base part 120. The mainboard 129, on one hand, is connected with a cable leading out from the mobility tube (including a cable for picking up a signal of the Faraday disc and a high voltage lead wire of the mobility tube), and on the other hand, provides quick slots for the preamplifier module 133, the high voltage module 130, a control board and the like, for facilitating fixing, replacement and maintenance of the modules; the power supply module 127 is used to convert an alternating current into a direct current and to supply constant and steady DC operating voltages for the mainboard 129 and the like. The preamplifier module 133 is used to shape, filter and amplify the signal received by the Faraday disc; the high voltage module 130 is configured to provide a jump pulse for an ion gate, to provide a steady electric field in a migration region and between a grid and a disc, that is, between a suppressor grid and the Faraday disc; the heating module 132 is used to heat structures of the gas chromatography-ion mobility spectrometer working in a high temperature condition; and the control module 132 is used to modify and control for heating, on-off of the apparatus and others parameters.

In one embodiment, the circuit control part of the gas chromatography-ion mobility spectrometry apparatus 100 is shielded by a shielding case. The shielding case may include, for example, a shielding housing for heating of the mobility tube, a shielding sleeve for the Faraday disc, a shielding housing for the whole mobility tube, a shielding housing for the high voltage module, a shielding housing for the preamplifier module and the like, such a multi-layer metal shield may effectively reduce interferences in collecting and outputting signals of the mobility tube from the outside and from internal circuits of the gas chromatography-ion mobility spectrometer, and the circuits are shielded such that external interference on operating stability of the circuits may be reduced, so that the mobility tube module may operate efficiently over a long time period.

As shown in the drawings, an AC power supply voltage is converted by the power supply module 127 into a low DC voltage, which may be directly supplied as constant and steady DC operating voltages for the mainboard 129, the control module 132, the high voltage module 130 and the preamplifier module 133. The high voltage module 130 is used to provide a jump pulse for an ion gate, to provide a steady electric field in a migration region and between a grid and a disc (that is, between a suppressor grid and the Faraday disc); the preamplifier module 133 is used to shape, filter and amplify the signal received by the Faraday disc; the central control board is used to modify and control parameters for heating, on-off of the apparatus and other parameters s. A fix post 128 is provided to fix the mainboard 129 onto the buffer base part 120. The mainboard 129 provides quick slots for the high voltage module, the preamplifier module, the central control board and the like, for facilitating installation and maintenance of the circuits, and meanwhile, inputs a high voltage for operation of the mobility tube into an electrode of the mobility tube, and transmits the signal of the Faraday disc to the preamplifier module 133, so that the signal is shaped, filtered and amplified by the preamplifier module. In an example, in order to avoid the signal from being interfered by the high voltage and avoid the signal of the Faraday disc from being interfered during being transmitted, shielded coaxial cables 135 are used as a high voltage lead wire between the mainboard 129 and the electrode of the mobility tube and a lead wire between the signal of the Faraday disc and the mainboard 129; meanwhile, the high voltage module 130 and the preamplifier module 133 are shield by a high voltage shielding case 131 and a preamplifier shielding case 134 respectively, and the mobility tube is wrapped by a mobility tube shielding aluminum skin 108, such that the shielded cables and the shielding cases can effectively reduce external electromagnetic interference on the mobility tube and the circuits, thus the detector system may operate efficiently for a long time. The buffer chambers provided by the buffer base part 120 may effectively eliminate gas flow pulse from the diaphragm pump 121, and can achieve independent control of migration gas and discharged gas in the positive and negative modes; on the other hand, the buffer base part may also provide quick interfaces for gas paths of the molecular sieve 12, the multicapillary column-ion mobility spectrometer 100 and the like, for facilitating replacement of the molecular sieve and connections of the gas paths. Meanwhile, the multicapillary column-ion mobility spectrometer 100, the molecular sieve 124, the power supply module 127, the heating module 126, the air pump 125, the mainboard 129 and the like are fixed on the buffer base part 120, thus the system may be formed into an integral module, such that the buffer base part 120 may be removed directly from the apparatus housing 136 during maintenance and installation, or may be reinstalled into the apparatus housing 136 after finishing installation and debug, which not only facilitates assembly, maintenance and replacement of the detector in the housing 136, but also provides better anti-vibration and shielding effects.

In other embodiments of the present disclosure, the gas chromatography-ion mobility spectrometry apparatus may be further provided with a combination one-way seal valve at a gas inlet of the housing 136 and a switch valve at a gas discharge outlet of the apparatus, such that automatic or manual seal of the whole gas path may be obtained during shutdown and transportation of the apparatus so as to achieve seal protection of the gas paths of the detector. In order to avoid that the clean gas path of the detector is contaminated by the external environment during long time shut down and transportation of the apparatus and the gas path needs to be purified for a long time in reuse of the apparatus, the valve 123 may be closed to disconnect the gas path the back gas pipe, and a son-mother head of a combination value 117 is closed to form a seal and then is covered by a cap, such that the one-way value provides protection of the gas path system of the detector, shortening purification time for reuse.

Although some exemplary embodiments of the general concept of the present disclosure have been illustrated and described, it would be appreciated by those skilled in the art that various changes or modifications may be made to these embodiments without departing from the principles and spirit of the disclosure. Thus, the scopes of the present disclosure are defined in the claims and their equivalents.

What is claimed is:

1. A gas chromatography-ion mobility spectrometry apparatus, comprising a housing, an injection port mounted to and connected with the housing and configured for inputting a gas containing a sample, a multicapillary column configured for separation of a gas substance and an ion mobility tub configured for analysis of the gas substance; wherein the gas chromatography-ion mobility spectrometry apparatus further comprises:
   a gas path part connected with the ion mobility tube and configured for providing the gas to the ion mobility tube and receiving a gas discharged from the ion mobility tube; and
   a buffer base part detachably mounted to the housing and configured to isolate vibration from outside the buffer base part, the ion mobility tube being disposed on the buffer base part, wherein the gas path part is mounted in an interior space of the buffer base part.

2. The gas chromatography-ion mobility spectrometry apparatus according to claim 1, further comprising a circuit control part configured to control operation of the gas chromatography-ion mobility spectrometry apparatus, wherein the whole circuit control part is disposed on a portion of the buffer base part above the interior space and arranged such that it is separatable from the gas path part.

3. The gas chromatography-ion mobility spectrometry apparatus according to claim 2, wherein the circuit control part is shielded by a shielding case.

4. The gas chromatography-ion mobility spectrometry apparatus according to claim 1, wherein the gas path part has a chamber configuration including a first buffer chamber and a second buffer chamber, which are in communication with a negative-mode discharge gas interface and a positive-mode discharge gas interface of the ion mobility tube respectively, so as to receive gas discharged from the negative-mode discharge gas interface and the positive-mode discharge gas interface respectively.

5. The gas chromatography-ion mobility spectrometry apparatus according to claim 4, wherein the gas path part further comprises a third buffer chamber, at least part of the gas discharged from the first buffer chamber and the second buffer chamber flows into the third buffer chamber, and at least a part of the gas discharged from the third buffer chamber is inputted as an auxiliary injection gas into the ion mobility tube.

6. The gas chromatography-ion mobility spectrometry apparatus according to claim 5, wherein the gas path part further comprises a molecular sieve disposed upstream of the third buffer chamber such that the gas discharged from the first buffer chamber and the second buffer chamber flows into the third buffer chamber after being filtered and purified by the molecular sieve.

7. The gas chromatography-ion mobility spectrometry apparatus according to claim 5, wherein the gas path part further comprises a first diaphragm pump and a second diaphragm pump respectively located downstream of the first buffer chamber and the second buffer chamber and respectively connected with the first buffer chamber and the second buffer chamber.

8. The gas chromatography-ion mobility spectrometry apparatus according to claim 7, wherein the first buffer chamber, the second buffer chamber and the third buffer chamber are sealable independently by means of valves.

9. The gas chromatography-ion mobility spectrometry apparatus according to claim 5, wherein the volume of the third buffer chamber is at least five times of the volume of the ion mobility tube.

10. The gas chromatography-ion mobility spectrometry apparatus according to claim 4, wherein volumes of the first and second buffer chambers are at least five times of the volume of the ion mobility tube.

* * * * *